United States Patent
Srivastava et al.

(10) Patent No.: US 8,114,264 B2
(45) Date of Patent: Feb. 14, 2012

(54) METHOD OF ELECTROPLATING A CONVERSION ELECTRON EMITTING SOURCE ON IMPLANT

(75) Inventors: Suresh C. Srivastava, Setauket, NY (US); Gilbert R. Gonzales, New York, NY (US); Radoslav Adzic, East Setauket, NY (US); George E. Meinken, Middle Island, NY (US)

(73) Assignee: Brookhaven Science Associates, Upton, NY (US)

( * ) Notice: Subject to any disclaimer, the term of this patent is extended or adjusted under 35 U.S.C. 154(b) by 955 days.

(21) Appl. No.: 11/758,914

(22) Filed: Jun. 6, 2007

(65) Prior Publication Data

US 2010/0137970 A1    Jun. 3, 2010

Related U.S. Application Data

(63) Continuation-in-part of application No. 11/351,435, filed on Feb. 9, 2006, now abandoned.

(60) Provisional application No. 60/652,129, filed on Feb. 10, 2005.

(51) Int. Cl.
    *C25D 3/30*        (2006.01)
    *C25D 5/02*        (2006.01)
(52) U.S. Cl. ........................ 205/300; 205/122
(58) Field of Classification Search .............. 205/128, 205/130, 131, 118, 122, 300; 204/297.01, 204/297.14
    See application file for complete search history.

(56) References Cited

U.S. PATENT DOCUMENTS

| | | | | |
|---|---|---|---|---|
| 3,575,826 A | * | 4/1971 | Bellinger et al. | 205/303 |
| 3,833,486 A | * | 9/1974 | Nobel et al. | 205/291 |
| 4,000,047 A | * | 12/1976 | Ostrow et al. | 205/253 |
| 4,412,892 A | * | 11/1983 | Chen et al. | 205/216 |
| 5,059,166 A | | 10/1991 | Fischell et al. | 600/3 |
| 5,302,168 A | | 4/1994 | Hess | 600/3 |
| 5,411,466 A | | 5/1995 | Hess | 600/3 |
| 5,484,384 A | | 1/1996 | Fearnot | 600/3 |
| 5,730,698 A | | 3/1998 | Fischell et al. | 600/3 |
| 5,824,045 A | * | 10/1998 | Alt | 623/1.15 |
| 5,879,282 A | | 3/1999 | Fischell et al. | 600/3 |
| 6,077,413 A | * | 6/2000 | Hafeli et al. | 205/170 |
| 6,187,037 B1 | | 2/2001 | Satz | 623/1.34 |

(Continued)

OTHER PUBLICATIONS

International Search Report and Written Opinion of the International Searching Authority, application No. PCT/US2008/065243, dated Dec. 8, 2008.

*Primary Examiner* — Luan Van (74) *Attorney, Agent, or Firm* — Wood, Herron & Evans, LLP (57) ABSTRACT

Methods for preparing an implant coated with a conversion electron emitting source (CEES) are disclosed. The typical method includes cleaning the surface of the implant; placing the implant in an activating solution comprising hydrochloric acid to activate the surface; reducing the surface by $H_2$ evolution in $H_2SO_4$ solution; and placing the implant in an electroplating solution that includes ions of the CEES, HCl, $H_2SO_4$, and resorcinol, gelatin, or a combination thereof. Alternatively, before tin plating, a seed layer is formed on the surface. The electroplated CEES coating can be further protected and stabilized by annealing in a heated oven, by passivation, or by being covered with a protective film. The invention also relates to a holding device for holding an implant, wherein the device selectively prevents electrodeposition on the portions of the implant contacting the device.

16 Claims, 4 Drawing Sheets

U.S. PATENT DOCUMENTS

| | | | |
|---|---|---|---|
| 6,322,490 B1 | 11/2001 | Stack et al. | 600/3 |
| 6,322,686 B1 * | 11/2001 | Brown et al. | 205/253 |
| 6,379,380 B1 | 4/2002 | Satz | 623/1.15 |
| 6,383,217 B1 | 5/2002 | Satz | 623/1.34 |
| 6,503,477 B1 | 1/2003 | Srivastava et al. | 424/1.65 |
| 6,635,082 B1 * | 10/2003 | Hossainy et al. | 623/1.15 |
| 6,638,205 B1 * | 10/2003 | Chan et al. | 600/3 |
| 7,022,136 B2 | 4/2006 | Lundqvist | 623/1.42 |
| 7,045,116 B2 | 5/2006 | Simon et al. | 424/9.1 |
| 7,198,675 B2 * | 4/2007 | Fox et al. | 118/500 |
| 7,208,070 B2 * | 4/2007 | Swain | 204/286.1 |
| 7,407,508 B2 * | 8/2008 | Kitaoka et al. | 623/1.15 |
| 2002/0183581 A1 | 12/2002 | Yoe et al. | 600/3 |
| 2003/0036699 A1 | 2/2003 | Strauss | 600/436 |
| 2003/0134142 A1 | 7/2003 | Ivey et al. | 428/646 |
| 2003/0233141 A1 | 12/2003 | Israel | 623/1.15 |
| 2004/0184989 A1 | 9/2004 | Thakur | 424/1.11 |
| 2005/0051437 A1 | 3/2005 | Kurashina et al. | 205/143 |
| 2005/0060021 A1 | 3/2005 | O'Brien et al. | 623/1.15 |
| 2005/0134142 A1 | 6/2005 | Yetter et al. | 310/311 |
| 2005/0288869 A1 | 12/2005 | Kroll et al. | 702/19 |
| 2006/0041182 A1 * | 2/2006 | Forbes et al. | 600/12 |
| 2007/0068823 A1 | 3/2007 | Takizawa et al. | 205/300 |
| 2007/0071676 A1 | 3/2007 | Gonzales et al. | 424/1.49 |

* cited by examiner

METHOD OF ELECTROPLATING A CONVERSION ELECTRON EMITTING SOURCE ON IMPLANT

CROSS-REFERENCE TO RELATED APPLICATIONS

This is a continuation-in-part of U.S. application Ser. No. 11/351,435, filed Feb. 9, 2006, now abandoned which claims the benefit of U.S. Application No. 60/652,129, filed Feb. 10, 2005, the entire content of each of which is hereby incorporated by reference thereto.

STATEMENT OF GOVERNMENT INTEREST

This invention was made with Government support under contract number DE-AC02-98CH10886, awarded by the U.S. Department of Energy. The Government has certain rights in the invention.

FIELD OF THE INVENTION

The invention relates generally to an electrodeposition process and product produced therefrom. More specifically, the invention relates to electrodeposition of a radioactive material on medical implants.

BACKGROUND OF THE INVENTION

A number of percutaneous intravascular procedures have been developed for treating stenotic atherosclerotic regions of a patient's vasculature to restore adequate blood flow. A common treatment is angioplasty, also known as percutaneous transluminal angioplasty (PTA). PTA is a non-surgical procedure that involves threading a flexible shaft into an artery and briefly inflating a balloon catheter that stretches the blood vessel open and squeezes away the obstruction. PTA, however, is only a partial solution in treating vascular diseases. Further, PTA and other known procedures for opening stenotic regions are associated with formation of plaque in blood vessels and frequent occurrences of restenosis, a re-closing of arteries as a result of injury to the arterial wall during the angioplasty procedure that can necessitate repeat angioplasty procedures or bypass surgery. Long-term restenosis can cause symptoms such as chest pain and fatigue, and increases the danger of heart attack, stroke, and kidney failure, while exposing patients to continued risks of thrombogenesis (blood clotting) and atherosclerosis (hardening of the arteries). It can also lead to recoil, i.e., the mechanical collapse of dilated vessel segment in response to vascular injury.

Restenosis is believed to be caused by smooth muscle cell proliferation or neointimal proliferation known as "hyperplasia" in the vessel wall, a repair response of the body prompted by the arterial trauma resulting from angioplasty. This hyperplasia of smooth muscle cells narrows the lumen opened by angioplasty. Restenosis is also believed to be caused by elastic recoil, the contraction of the vessel wall to its previous position after having been stretched by balloon angioplasty, and by vessel wall remodeling, the formation of scar tissue in the region traumatized by balloon angioplasty. Treatment of restenosis has therefore focused on inhibiting hyperplasia of smooth muscle cells and vessel wall remodeling, and on preventing recoil closure of arteries with an implant.

To inhibit hyperplasia of smooth muscle cells, intravascular radiotherapy has been used. Radiation is commonly used to treat catastrophic diseases such as cancer because of its effectiveness in reducing hyperproliferation of cancerous cells. Localized radiation inhibits cellular proliferation, including smooth muscle proliferation, and has been shown to inhibit, the typical wound healing process. It is believed that radiation breaks down genetic material in the vascular endothelium, causing cell death (apoptosis) and preventing cellular division. A dose-dependent hyperplastic response and a marked reduction in smooth muscle cell build-up have been observed with intravascular radiotherapy.

Thus, attempts have been made to deliver radiation doses with a radioactive implant, such as a radioactive stent. In a radioactive stent, activated radioisotopes are typically either placed inside the stent, alloyed into the metal from which the stent is made, or coated onto the exterior surface of the stent. A radioactive stent is advantageous in that it can obviate the disadvantages associated with catheter-based brachytherapy, such as prolonged insertion of a large intracoronary catheter, which can induce ischemia, and administration of a high dose of a radioactive source to the deep vessel wall, which increases the risk of overexposure to radiation for both patients and physicians. Because the radioactive source is located on the device itself and is implanted right at the site of the lesion, a radioactive stent reduces the risk of inadequate positioning or coverage.

Common sources of radiation used on radioactive stents include pure beta emitting radioisotopes such as phosphorus-32 and yttrium-90. A fundamental problem with pure beta emitting radioactive sources, however, is that radioactivity cannot be precisely calibrated in the microcurie range in a typical catheterization laboratory setting using a conventional well counter as a dose calibrator. Further, uniform in-situ implantation, such as sputter coating, plating or ion deposition of phosphorus-32, which has a 14.3-day half-life, on a stainless steel surface, is complex and problematic. Ion deposition or implantation of stable isotope is a line-of-sight process, and, as a result, the radioactive coating and the iso-dose/radiation field it produces may not be uniform on the outer circumference, resulting in considerable variation in the radiation dose emitted and delivered to tissue. Moreover, common beta emitters have excessively long ranges of radiation, delivering 95% of the radiation dose within 4 mm of the stent, far more than 100 to 250 micrometers, measured from the intimal layer edge inward towards the external edge of the coronary artery, usually needed to inhibit proliferation of inflammatory cells in coronary arteries. Such excessive irradiation is undesirable and results in unwanted effects, such as weakening of arterial walls and cellular damage.

For example, U.S. Pat. No. 6,187,037 discloses a metal stent for vascular implantation comprising a generally tubular structure whose external surface is adapted to engage the interior vascular surface when implanted, with the metal of the stent containing a substantially uniform dispersion of from about 0.05 to about 10 percent by weight of one or more naturally occurring or enriched stable isotopes having a half-life of less than two months and that are principally beta particle emitters, so that when activated, the stent emits low to moderate dosages of radiation uniformly to reduce cell proliferation.

As an alternative to beta emitting radioisotopes, radioactive tin (Sn-117m, also referred to as tin-117m or $^{117m}$Sn) has been contemplated because of its short range of emission, which reaches about 0.2 to 0.3 mm in tissue, and the monoenergetic nature of its conversion electron emission. Plating radioactive tin on a metal implant, however, has required a complex process with pronounced drawbacks imposed by tin's radioactivity and a high chloride concentration in the plating solution that is required to dissolve the tin. Because of the specific activity (the number of decays per second per amount of substance) of Sn-117m, which typically ranges between 250 to 5000 mCi per mg (with no carrier added) from accelerator production, to about 2 to 25 mCi per mg of stable tin-117/118 from reactor production, a tin plating solution cannot practically contain more than $10^{-4}$ to $10^{-2}$ M $^{117}Sn^{2+}$, which is several orders of magnitude than the optimal tin plating concentration required in a conventional tin plating process. In addition, to dissolve radioactive tin, the plating solution must maintain a high concentration of chloride, e.g., in the form of tin tetrachloride dissolved in hydrochloric acid, at a level of about $10^{-1}$M, in contrast to the chloride concentration used in a plating solution for regular, non-radioactive tin, which is generally kept below 100 ppm. It would be advantageous to provide a process that facilitates radioactive tin plating.

U.S. Pat. No. 6,638,205 discloses a radioactive medical device comprising a radioactive, electroplated substrate coated with at least one layer of polymer and sealed in a jacket layer. The one or more layers of polymer and jacket are provided to reduce leaching of a radioactive element from the electroplated substrate. The radioactive medical device is useful for radiation therapy of diseased tissue such as cancers and especially malignant tumors. P-32, S-35, Cl-36, Sc-47, Cu-67, Y-90, Mo-99, Pd-103, Sn-117m, I-123, I-124, I-125, I-129, I-131, Ce-144, Ho-166, Re-186, Re-188, W-188, Ir-192, and Au-199 are stated as being possible radioactive isotopes while the amount of radioactivity that is provided by such devices in is the range of about 100 to 200 $mCi/mm^2$. The use of the outer layers suggests concern over the quality of adherence of the radioactive isotope to the device. Again, a process that facilitates deposition of radioactive tin coatings is needed.

Thus, there is a need to address the shortcomings of current intravascular radiotherapy technology, including inconsistent dose administration, excessive irradiation of beta emitter therapy, and various procedural shortcomings in designing and preparing implants to deliver radiation to a subject. The present invention now overcomes these shortcomings.

SUMMARY OF THE INVENTION

The invention provides methods for electrodepositing a coating of a conversion electron emitting source (CEES) upon an implant, which comprises activating a surface of the implant to receive the coating; and contacting the activated surface of the implant with an electroplating solution comprising ions of the CEES, an electrolyte, surfactant, and antioxidant molecules under conditions sufficient to provide a coating of the CEES upon the surface of the implant, wherein the coating provides radiation from conversion electrons at a specific emission distance from the surface of the implant.

Advantageously, the activating solution comprises hydrochloric acid; the electroplating solution comprises HCl and $H_2SO_4$ as the acid; gelatin, phenol-sulfonic acid or di-hydroxybenzene hydroxybenzene serve as surfactants; and resorcinol or similar compounds as the antioxidant. In these solutions, the HCl is present in an amount of about 0.1 to 6 M, the $H_2SO_4$ is present in an amount of about 0.1 to 1M, the antioxidant resorcinol and the surfactant gelatin are present each in an amount of about 1 to 10 g/l.

The method also comprises providing $H_2$ evolution during the electroplating, which enhances mass transfer of the reacting species. In addition, the electroplated coating can be annealed, passivated, or covered with a protective film for further protection.

According to an embodiment, the radiation to be delivered is controlled so that the radioactivity per unit area emitted by the coated implant is less than about 10 $mCi/mm^2$. In addition, the coated implant emits conversion electrons to a distance of about 0.2 to 0.3 mm into tissue when the implant is placed in a body lumen, thus avoid damage to tissue that is located further away than these distances.

The invention has wide applicability to various implants, including metal stents. For example, a metal stent comprising stainless steel, a shape-memory alloy, or a combination thereof, can be coated with a CEES comprising $^{117m}Sn$ by performing electrodeposition in an electroplating solution comprising about $1 \times 10^{-5}$ to $1 \times 10^{-2}$M $Sn^{2+}$, about 0.1 to 6 M HCl, about 0.1 to 1 M $H_2SO_4$, and about 1 to 10 g/l of at least one of resorcinol and gelatin, at a current density of 5 to 100 $mA/cm^2$ for 0.5 to 5 minutes at room temperature.

The method further comprises forming a seed layer on the activated surface of the implant prior to contacting that surface with the electroplating solution. When this optional seed layer is desired, it can be formed with metal ions that are present in the activating solution or provided after the activation step. The metal ions used to form the seed layer should nucleate on the substrate more easily than the CEES. For example, cobalt, nickel or copper ions, or a combination thereof can be used with a stainless steel implant and a CEES comprising $^{117m}Sn$.

According to an embodiment, an implant holding device is used during the electrodeposition, wherein the holding device prevents electrodeposition on a surface of the implant contacting the holding device. For example, where the implant is a stent having interior and exterior surfaces and contacts the holding device along its entire interior surface, the holding device essentially prevents electrodeposition on the interior surface of the stent such that only the exterior surface is electroplated.

Thus, by using such a holding device, the invention also provides a method for selectively electroplating an implant. In an embodiment, the holding device has a tweezers-like shape, with a body and at least two elongated arms extending from the body, such that the implant is mounted around and encircles the aims. This device represents another embodiment of the invention.

BRIEF DESCRIPTION OF THE DRAWINGS

The invention is more fully appreciated upon a review of the following detailed description and drawings, in which.

DETAILED DESCRIPTION OF THE PREFERRED EMBODIMENTS

The invention provides simple and effective methods for plating an implant with a conversion electron emitting source (CEES). Conversion electron emission is a unique form of radiation with low toxicity and specific physicochemical properties. A conversion electron is an electron ejected from the atom in the process of internal conversion, a photophysical process that produces an isoenergetic radiationless transition between two electronic states of the same multiplicity. When the transition results in a vibrationally excited molecular entity in the lower electronic state, the entity usually undergoes deactivation to its lowest vibrational level, provided that the final stage is not unstable to dissociation. Because conversion electron emission generally has low energy and short emission range in tissue, it would be advantageous to utilize CEES on an implant such as a stent that is used in a body lumen, such as a blood vessel. Furthermore, a conversion electron emitting coating on an implant does not prevent growth of a thin layer of endothelial cells on the implant, thus providing a smooth inner cover to incorporate the implant into the body lumen. Such endothelization helps prevent subsequent thrombosis and restenosis of the artery or other blood vessel.

Any suitable CEES or combinations of CEESs capable of being electroplated can be used. A preferred example of such CEES is $^{117m}$Sn, which delivers conversion electrons at a short range and monoenergetic radiation that has significant anti-neoplastic properties in high concentrations. $^{117m}$Sn is usually in metallic form and can be prepared in an accelerator, such as a cyclotron, by transmutation of antimony into no-carrier-added $^{117m}$Sn by high energy proton induced nuclear reactions. In small doses, conversion electrons from $^{117m}$Sn produce an anti-inflammatory cellular response to inhibit excess accumulation of cells around the implant plated with $^{117m}$Sn. $^{117m}$Sn has a half-life of 14 days and emits conversion electrons with energies of 0.13 MeV and 0.15 MeV, with no average because of the discrete energy delivery from conversion electrons. $^{117m}$Sn conversion electrons are delivered to a distance between 0.22 mm and 0.29 mm in tissue. Since twenty-eight days, corresponding to two half-lives of $^{117m}$Sn, is believed to be about the optimum period for neoproliferative tissue suppression and suppression of neointimal proliferation following angioplasty and other primary interventional treatments in the coronary arteries and other vasculature, radiotherapy with $^{117m}$Sn can provide highly effective treatment, while significantly limiting any damage to underlying tissue because of its low-energy conversion electron emission and short emission range in tissue. Further advantageously, such limited energy delivery prevents excessive cell growth at either end of the implant, known as the "candy wrapper" effect, which is observed with a conventional radioactive stent.

Any implant comprising a substrate that can be electroplated with the desired CEES can be used. In an embodiment, the substrate comprises a solid metal body portion made from a metal or alloy. Alternatively, the substrate can comprise metallic and non-metallic portions, of which the non-metallic portions can be coated or encapsulated with metal. Examples of metallic substrates that can be used according to the invention include, but are not limited to, steels such as stainless steel, platinum, shape-memory alloys such as nitinol (nickel titanium alloy), tin, silver, bronze, zirconium, aluminum, brass, zinc, titanium, tantalum, rhodium, and palladium. Any metal material that is compatible with the physiological environment into which the implant is to be placed can be used. In a preferred embodiment, stainless steel is used.

The metal substrate can also include portions made of the CEES. For example, when $^{117m}$Sn is used as the CEES, the metal substrate can be formed, partially or entirely, of tin, including $^{115}$Sn, $^{117}$Sn, other stable forms of tin, and combinations thereof.

The implant and the substrate can be any shape, design, and dimension. For example, the substrate can comprise a tube, wire, disk, seed, or ribbon configuration, or a combination thereof. The implant is preferably configured and dimensioned to conform to the body lumen to which the implant is inserted, such that at least a portion of the implant contacts a surface of the lumen. Thus, the implant can be used in any body lumen where radiotherapy is desired, including blood vessels, ureters, urethras, arteriovenous dialysis shunts, microvascular arteries, arterioles, veins and venules (especially macular and meningorachidian vessels), vaginal canal, cervical canal, esophagus, trachea, bronchioles, bronchi, gastrointestinal tract, ostomies, biliary and pancreatic ducts, and the like. In a preferred embodiment, the implant is a stent or graft having an expandable scaffold structure, such that it is delivered to the target site, i.e., a body lumen such as an organ or a blood vessel, in a collapsed, non-expanded configuration and is expanded in situ at the target site to an expanded configuration.

Depending upon the configuration of the implant, the electrodeposited CEES coating can be made completely or partially upon some or all exposed surfaces of the implant. For example, the surface or surfaces of the implant that will contact tissue can be coated with the CEES deposit, while other surface portions that are not in contact with tissue do not need to be provided with the coating. This enables the conversion electrons to be provided into the tissue, while exposed surfaces are uncoated.

According to one embodiment of the invention, the electroplating method comprises the steps of cleaning the implant if desired or necessary; activating the surface of the implant to be plated; and then plating the activated surface with a CEES coating, e.g., $^{117m}$Sn. The CEES coating can be directly plated on the activated surface. Alternatively, before plating the CEES coating, a thin "seed" layer of metal can be deposited on the activated surface to generate nucleation sites for CEES deposition. The metal forming the seed layer is selected to nucleate the surface more easily than the CEES, so that the CEES bonds to the seed layer more easily than direct bonding to the implant. The seed layer can be formed simultaneously with, or after, the activation of the surface. After electroplating the implant with the CEES, the CEES film coated implant can optionally be further treated to provide additional protection against damage or dissolution of the CEES film. Any suitable treatment can be used, including an additional protective layer and passivation of the CEES film.

Preferably, the implant to be electroplated should be very clean before electrodeposition to facilitate electroplating of the CEES coating. The implant can be cleaned by thorough rinsing with an organic solvent such as acetone or ethyl alcohol, optionally with sonication, to remove any adventitious grease and dust particles. Other known cleaning techniques can be used if desired.

The surface of the implant is then activated to receive the CEES coating. Generally, this is accomplished by immersion of the surface to be plated in an acid or other suitable oxidizing or activating solution. When a steel or stainless steel implant is used, activation is obtained by contacting the surface with dilute HCl solution for a suitable period of time, followed by rinsing. This is conveniently accomplished by immersing the implant into the acid. The HCl concentration is typically at least about 0.1 M, more preferably at least about 1 to 2 M. The implant is immersed in the HCl solution for at least about 5 seconds, preferably at least about 10 seconds, and more preferably at least about 20 seconds. The implant is immersed for at most about 150 seconds, preferably at most about 100 seconds, and more preferably at most about 50 seconds. In a preferred example, the immersion time is about 30 seconds. After immersion, the implant is rinsed using any suitable rinsing procedure, for example, rinsing with water and alcohol or by applying $H_2$ evolution in $H_2SO_4$ to reduce remaining oxides, followed by rinsing with water and alcohol. For example, a typical vascular stainless steel stent can be rinsed by performing $H_2$ evolution in 0.1 to 3 M $H_2SO_4$, for about 1 to 5 min at a current of 20 to 100 mA per stent. Alternatively, activation involves, anodic activation in 1M $H_2SO_4$ with a current of 50 mA/cm$^2$ during 60 sec, followed by immersion in 1M HCl during 20 sec and cathodic reduction in 1 M $H_2SO_4$ at 25 mA/cm$^2$, 30 sec.

Simultaneously with or after the activation, the implant is optionally treated to generate nucleation sites on the surface by forming a "seed" layer. For steel or stainless steel implants, the activation and the seed layer formation can be performed simultaneously by using a solution that contains HCl, to dissolve passive film on the implant, and metal ions that nucleate on the implant more easily than the CEES. Alternatively, a seed layer can be formed after the activation by using a separate solution containing metal ions that nucleate on the implant more easily than the CEES. For example, to generate nucleation sites on a stainless steel implant to be plated with $^{117m}$Sn, Co, Ni, and/or Cu metal ions ($Co^{2+}$, $Ni^{2+}$, $Cu^{2+}$), which nucleate on steel more easily than Sn, can be deposited to form a seed layer on the steel substrate. Such Co, Cu, and/or Ni seed layer provides better bonding of Sn than direct bonding of Sn to steel.

In another example, a Co seed layer is formed simultaneously with activation of the surface of the substrate by immersing the substrate in a 1M HCl solution containing 0.5M $CoCl_2$ for 1 to 3 minutes, at a current density of 5 to 10 mA/cm$^2$. In another example, a Ni seed layer is formed simultaneously with activation by immersing the substrate in a 2M HCl solution containing 0.1 to 0.2M $NiCl_2$ for about 1 to 3 minutes at a current density of 5 to 15 mA/cm$^2$. In another example, a Cu seed layer is formed simultaneously with activation by immersing the substrate in a 2M HCl solution containing 0.1 to 0.2 M $CuCl_2$ for about 1 to 3 minutes at a current density of 5 to 15 mA/cm$^2$.

Deposition of a seed layer is followed by rinsing of the substrate with water, after which the substrate is transferred to the CEES plating solution. With or without the seed layer, the present electroplating method provides smooth deposit of the CEES while minimizing deposition of the CEES on surfaces where coating is not desired, e.g., the inner surface of a stent, by performing electroplating under diffusion control for short times with $H_2$ evolution and strong adsorption of gelatin, and by optionally using a holding device that prevents the electroplating solution from contacting certain surfaces of the implant.

In an embodiment for depositing $^{117m}$Sn directly on a stainless steel stent without a seed layer, about $1\times10^{-5}$ to $1\times10^{-2}$M $Sn^{2+}$ is used in a solution containing about 0.1 to 1M $H_2SO_4$, about 0.1 to 6 M HCl, and about 1 to 10 g/l of gelatin, using galvanostatic deposition with a current density of 5 to 100 mA/cm$^2$, at room temperature (about 20 to 25° C.) for 0.5 to 5 minutes. In a further example, $^{117m}$Sn is plated from a 1 to $5\times10^{-3}$M solution in 1.2 M HCl/0.2M $H_2SO_4$ containing about 4 mg/ml of gelatin, using galvanostatic deposition with a current of 30 mA per stent, at room temperature for 0.5 to 5 minutes. The electroplating parameters and conditions can be adjusted depending on the amount of CEES to be deposited.

When plating the CEES over a seed layer, the seed layer-plated implant is placed in the electroplating solution and the potential or current is promptly applied to avoid significant dissolution of the seed layer. Optionally, the stent (electrode) can be immersed in the electrolyte under applied voltage (potential) that will produce a desired cathodic current, thus precluding any dissolution of the seed layer.

In an embodiment for depositing $^{117m}$Sn on a stainless steel stent over a seed layer, a plating solution containing about (1 to 8)×10$^{-3}$M $Sn^{2+}$; about 0.1 to 1M, and preferably 0.2 M, $H_2SO_4$; an amount of HCl remaining from Sn dissolution, about 0.1M; and about 1 to 10 g/l, preferably about 2 g/l, of resorcinol and/or gelatin are used, using potentiostatic or galvanostatic deposition at room temperature at a potential of E=−0.5 to −1.2V, versus the Ag/AgCl/Cl$^-$ reference electrode, and a current of 0.1 to 25 mA/cm$^2$.

With or without a seed layer, argon or $N_2$ bubbling may be used to enhance mass transport and help compensate for the adverse effects of low $Sn^{2+}$ concentration of the electroplating solution on the quality of the Sn coating by allowing greater adhesion and smoothness.

Thus, the present methods provide effective electrodeposition of CEES such as $^{117m}$Sn despite low CEES (e.g., $Sn^{2+}$) concentration in the electroplating solution necessitated by the specific radioactivity of the CEES. A skilled artisan will also appreciate that the efficiency of the electroplating reaction is affected by parameters such as the volume of the electroplating solution, the depth of the submersion of the anode and cathode, the distance between the anode and cathode, and would adjust such parameters accordingly. A skilled artisan will also appreciate that parameters such as half reactions, current, voltage, and time of electroplating will vary depending on the type of the substrate material and the nature of the CEES being deposited on the substrate.

A current efficiency of 20 to 80% is usually obtained under the above conditions, because the redox reaction $Sn^{4+}+2e^-$ =$Sn^{2+}$ and $H_2$ evolution, which take place during the electrodeposition in addition to the Sn deposition reaction, decrease the current efficiency and the quality of the Sn coating. The rate of the $H_2$ evolution can be reduced by adding thallium (Tl$^+$) to the plating solution in the concentration range between $10^{-7}$ and $10^{-2}$ M. Thallium is a highly effective inhibitor of $H_2$ evolution, and its small deposition in a monolayer-limited range advantageously improves the quality of the Sn film.

To increase the $^{117m}$Sn$^{2+}$ concentration in the plating solution, irradiated tin-117 metal can be dissolved in concentrated HCl without the addition of stable ("cold") tin, followed by dilution with $H_2SO_4$. In an example, the concentration of $Sn^{2+}$ in such plating solution is about $1\times10^{-2}$M, while the concentration of HCl is about 2M.

When using stannic tin as the starting radioactive tin material, additional stable tin is preferably dissolved in concentrated HCl in the presence of radioactive tin, to establish an equilibrium such that the radioactive tin behaves like "cold" tin, i.e., both radioactive and stable tin are homogeneously distributed and act as $Sn^{2+}$. To achieve this, a weighed piece of high purity tin wire is placed in a dissolution vessel, along with an aliquot of radioactive tin and a volume of 12M hydrochloric acid to establish an equilibrium such that the radioactive tin behaves like the "cold" tin (as $Sn^{2+}$). Once the tin wire is completely dissolved, the solution is ready for use. Since tin readily oxidizes in air, the resulting $Sn^{2+}$ should not be allowed to stand in air any longer than necessary.

The quality of the tin coating can be checked by standard tests for bonding and adhesion, for example, by applying an adhesive tape (e.g., SCOTCH® tape) and bending a portion of the implant (e.g., wire constituting a stent implant) at 90 degrees. If the electroplated deposit does not peel off with the tape, or if no cracks occur upon bending, the adhesion of the coating is satisfactory.

The amount of radiation provided by an implant electroplated according to the invention will depend on the purpose of the implant. For example, where the implant is intended to reduce cell migration and endothelization or to stop all cell activity by destroying cells down to a depth of about 3 mm from the implant surface, $^{117m}$Sn can be plated as the CEES directly on a surface of the implant that contacts the wall of the body lumen being treated.

The amount of radioactivity loaded onto the implant can be varied by using CEES having the desired radioactivity, and/or by adjusting the concentration and amount of the CEES in the electroplating solution, electroplating reaction time, and other electroplating parameters. Preferably, the amount of CEES plated on the implant is such that the implant emits conversion electrons to a distance of at least about 0.1 mm, more preferably at least about 0.15 mm, and even more preferably at least about 0.2 mm in tissue. The implant emits conversion electrons to a distance of at most about 0.5 mm, preferably at most about 0.4 mm, and even more preferably at most about 0.3 mm in tissue. In a preferred example, the plated implant emits conversion electrons to a distance of about 0.2 mm to 0.3 mm in tissue.

In an embodiment, the CEES is $^{117m}$Sn and is plated on at least a portion of a metal stent in an amount sufficient to provide therapeutically effective radiation emission. Preferably, the radioactivity per unit area provided by $^{117m}$Sn is less than about 10 mCi/mm, and more preferably in the range of about 0.02 to 10 mCi/mm. Depending upon the total tin concentration of the electroplating solution that is considered appropriate, either the reactor-produced $^{117m}$tin (specific activity about 4 to 25 mCi/mg) or no-carrier-added (NCA) $^{117m}$Sn (specific activity about 200 to 5000 mCi/mg) can be used. Higher total tin concentrations in the solution can be easily achieved by combining NCA $^{117m}$Sn with appropriate amounts of the carrier stable tin (enriched or natural tin). Various desired total radiation emissions from the stent in the range from 0.02 µCi/mm to 2.75 µCi/mm preferably from 0.1 µCi/mm to 250 µCi/mm, and more preferably from 1.0 µCi/mm to 60.0 µCi/mm per stent can thus be provided using, as necessary, either the reactor-produced or the accelerator-produced NCA $^{117m}$Sn.

Further, while $^{117m}$Sn has a half-life of 14 days and an effective therapeutic time equal to two half-lives (28 days), the storage time of $^{117m}$Sn can be increased by increasing the purity of $^{117m}$Sn or by increasing the amount of $^{117m}$Sn adhered to the implant to allow for the radioactive decay. For example, plated implants expected to be stored before use can include proportionally larger amounts of $^{117m}$Sn to compensate for the radioactivity decay during storage.

If desired, the CEES coated implant is further treated to provide either a smoother surface of the coating and/or additional protection of the CEES film coating against dissolution and damage, such as cracking during implantation.

If necessary, the CEES metallic coating of $^{117/117m}$Sn can be polished and/or stabilized as necessary by annealing in an atmosphere of argon or nitrogen, within an oven, at about 100 to 300° C. This considerably smoothens the surface and makes it less damaging, for example during implant placement within sensitive structures such as within a coronary artery. The plated tin in this example can additionally be oxidized with air within an oven at similar temperatures to provide a smooth coating of the more biologically inert material, tin dioxide. Alternatively, the coating can be stabilized, smoothened, and made more biologically compatible by converting the top layer of Sn into $SnO_2$ by heating in air or $O_2$ as described above. The plated tin or other CEES material can also be protected by forming one or more layers of a thin protective film over the CEES coating. The protective film can be formed of any suitable material, including alkene thiol, methyl methacrylate, and noble metals such as gold, silver, platinum, tantalum, and palladium. Preferably, the protective film is transparent with respect to the emitted radiation, such that attenuation of radiation by the protective film layer is negligible. Further, the protective film preferably does not significantly alter the properties of the implant, such as pliability.

According to an example, the protective film is a self-assembled monolayer of alkene thiol. In another example, the protective film is a thin film of methyl methacrylate, which can be formed by immersing the implant in a dilute solution of methyl methacrylate. In yet another example, the protective film is a thin film of a noble metal, formed by electroless plating or by placing the implant in an anionic solution of cyanide, chloride, or other strongly complexing anions while controlling the potential. The protective film can be applied by any other suitable means, including dipping the implant in, or spraying or painting the implant with, a liquid that forms the protective film upon drying.

Furthermore, the protective film is provided at a thickness that is less than the conversion electron emission distance so that the conversion electrons are delivered to the tissue of the lumen. For example, since a tin-117m coated implant emits conversion electrons to an emission distance of about 0.2 to 0.3 mm, the coating thickness must be less than that distance so that the electrons can contact body tissue. The thickness of the coating can be customized based upon the therapeutic application. For example, a thin discrete and monoenergetic distribution would be preferable for inflammatory diseases such as the vulnerable plaques. Alternatively, if it is desirable to deliver high total energies over a longer range without regard to monoenergetic and discrete distribution, for example cancerous tissue, then a thicker electroplating can be performed. This can be done for any particular application to assure more precise delivery of the radiation to a desired location.

Alternatively, the CEES coating can be protected by passivation of the CEES film coating. For example, a tin film can be passivated by converting the topmost or exposed atomic layers of the film into $SnO_2$ by placing the implant into a weak acid solution (e.g., 1 M citric acid solution) for several seconds at −0.1 to 0.5V, or by annealing in air or O2 within an oven at 100 to 300° C., as described above.

The CEES coated implant according to the invention can be prepared such that the concentration of the CEES varies along the body of the implant. For example, relatively more or less radioactivity can be provided at terminal ends of the implant, or at portions of the implant contacting adjacent tissue requiring more irradiation. Such differential concentrations can be achieved by any suitable means, for example, by providing activation and/or seed layer to only a portion of the implant; placing only a portion of the implant in the electroplating solution; and/or covering a portion of the implant with a material or a device that blocks or reduces the contact of the electroplating solution with the implant.

Providing such differential concentrations of CEES on the implant can reduce the "candy wrapper" effect observed in conventional radioactive implants and provide selective radiation therapy. For example, differential distribution of radioactivity can preclude or reduce radiation at terminal ends of the implant such that only the tissue contacting the nonterminal portion of the implant is exposed to radioactivity. Alternatively, higher differential distribution of $^{117m}$Sn radioactivity at terminal ends of the implant would provide greater radiation exposure to the tissue around and adjacent the terminal ends. Such differential radioactivity is especially useful in treating inflammatory activity of tissue around the implantation site that does not need to actually contact the implant.

Also advantageously, the implant can be plated with a CEES over its entire surface area, or selectively or differentially over only certain portions of the implant. Thus, according to one embodiment, a CEES is plated over only an exterior surface of the implant that contacts the body lumen, or is provided on selected locations of the implant so that the implant delivers conversion electrons selectively, only from the plated areas.

For example, the implant is a metal luminal stent, such as a conventional stainless steel vascular stent having generally cylindrical inner and outer portions, and is plated with Sn-117m only on the outer surface so that conversion electrons are emitted only from the portions of the stent that contact the body lumen.

According to an embodiment, such selective or differential plating is achieved by using a holding device during electrodeposition.

Figure 1:
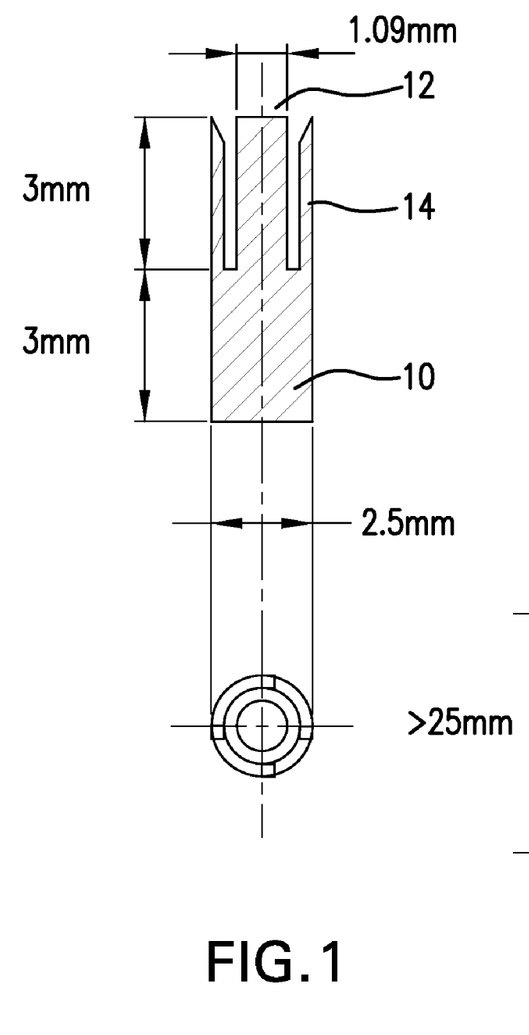
FIG. 1 is a schematic top and side illustration of a stent plating device and the required electrical contacts according to an embodiment of the invention.

Referring to FIG. 1, the holding device 10 has a center column 12, onto which implants are mounted, and two or more side arms 14 that are spaced apart from the center column 12. By adjusting the width of the center column and the distance between the center column and the side arms, the holding device can be made to contact only certain areas of the implant, to prevent the plating solution from contacting those areas. For example, when plating a stent having about 1 mm inner diameter (in unexpanded configuration), the center column of the holding device can contact, or is sufficiently close to, the interior of the stent, such that the center column prevents electrodeposition on the interior by physically covering the interior or by creating sufficient surface tension to prevent the plating solution from entering the area between the column and the interior of the stent. When the side arms are narrow and placed at a distance sufficiently spaced apart from the center column such that the electroplating solution flows into the area between the side arms and the exterior of the stent, the stent would be plated only on the exterior. Similarly, the holding device can be configured such that the interior of the side arms contacts the exterior of the stent and the center column is sufficiently narrow to permit the electroplating solution to flow into the cavity defined between the center column and the interior of the stent, resulting in a stent plated only on its inner surfaces.

Thus, the size and configuration of the holding device can be varied depending on the size and configuration of the implant and the desired selective coating. For example, when used with a luminal stent of conventional cylindrical design and an inner diameter of 1 mm, the diameter of the center column can be slightly less than 1 mm to contact the inner diameter of the stent, and full diameter of the holding device (from side-aim-to-side-arm) can be about 2.5 mm such that there is sufficient space between the exterior of the stent mounted on the center column and the side arms. The length of the holding device can also be adjusted as desired, depending on the application and the number of implants to be mounted on the holding device. A length of about 50 mm will typically accommodate multiple stents in a single electroplating process.

Figure 2:
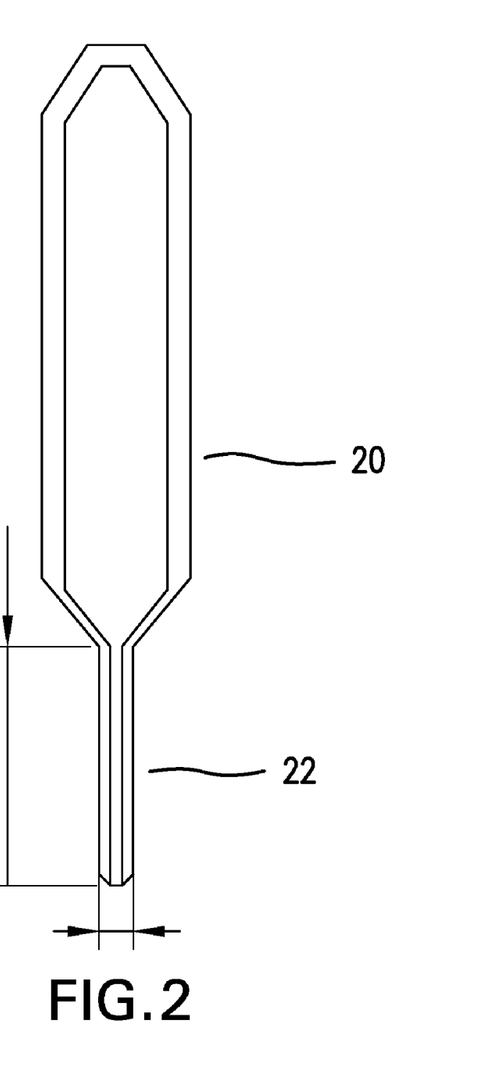
FIG. 2 is a schematic illustration of a stent holding device (stainless steel tweezers) according to another embodiment of the invention.

Another holding device according to the invention is shown in FIG. 2, wherein a tweezers-like device 20 includes elongated arms of forceps 22. The implant is mounted over the arms to encircle them. Any gap between the outer perimeter of the device and the interior of the implant is sufficiently close such that the device shields the interior of the implant from contacting the electroplating solution, for example, by surface tension. As a result, only the exterior of the implant is exposed to the electroplating solution and is coated during the electrodeposition. For example, when electroplating a stent having an unexpanded inner diameter of 1 mm, the diameter around the outer perimeter of the device around arms is slightly greater than 1 mm. The length of the holding device can be adjusted as desired. Again, a length of about 50 mm or greater will typically accommodate multiple stents in a single electroplating process.

Advantageously, even though the contact between the holding device and the implant is not airtight, the holding device according to the invention effectively blocks the electroplating solution from reaching the surfaces of the implant that contact the holding device. Without wishing to be bound by theory, it is believed that the holding device blocks electroplating by creating a very thin film of electrolyte with a very high resistance and a negligible amount of Sn ions that essentially preclude a significant Sn deposition on the inner side of a stent.

Further advantageously, the holding devices of the invention can also function as the electrical contact during electroplating. The holding devices can be made of any suitable material that is capable of acting as electrical contact and that does not adversely affect the electroplating process. An example of suitable material is stainless steel, which can be platinized for enhanced stability.

A skilled artisan will appreciate that the holding devices can include additional structural features, such as hooks for attaching or securing the holding device onto an electroplating cell. Further, while the present holding devices are described in connection with CEES electrodeposition, it will be appreciated that the devices can be used with any electroplating process to provide selective deposition.

Any suitable electroplating cell can be used to perform the present electroplating process, depending on the size and shape of the implant, the number of implants in a batch, and the electroplating parameters. The cell can have the conventional cylindrical design of various volumes, and can be made of any suitable material, including glass, metal, and polymer, such as TEFLON®.

Figure 3:
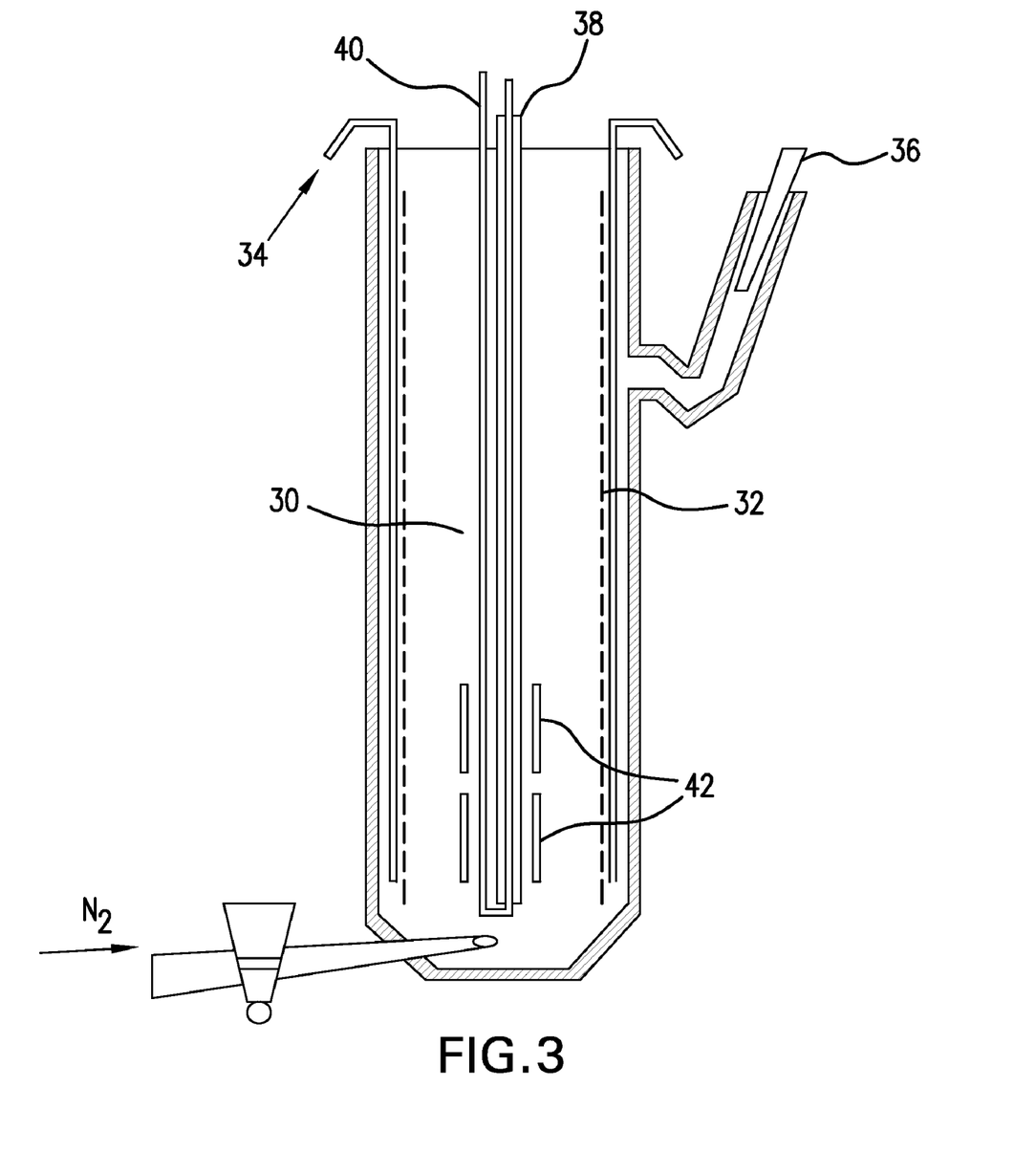
FIG. 3 is a schematic illustration of a glass electroplating cell for plating 10 to 15 stents according to the invention.

According to an example, a glass cylinder 30, as shown in FIG. 3, of about 20 to 40 ml volume is constructed to contain about 10 to 15 stents having a size and general shape typical of cardiovascular stents. The cylinder is about 20 cm long, and has anode and cathode compartments separated by a porous, hydrophilic polyethylene film 32. The anode 34 (counter electrode) consists of two Pt 5 mm ribbons, and an Ag/AgCl, Cl⁻ serves as the reference electrode 36. Stents 42 are mounted on a tube mandrel 38, e.g., TEFLON® tube mandrel, with a thin Pt wire 40 serving as electrical contact. Bubbling Ar or $N_2$ enhances mass transport during electrodeposition. Alternatively, the holding device in FIG. 2 can be used instead of mandrel.

According to another example, a miniature glass cell of 1 to 10 ml volume is constructed to electroplate a single stent. This cell is preferred when plating with a radioactive tin solution, i.e. a plating solution of irradiated tin-117 metal (containing radioactive tin-117m) dissolved in concentrated HCl without the addition of stable ("cold") tin, especially when directly plating tin on a substrate without a seed layer. The stent can be plated in an unexpanded configuration using a holding device.

Figure 4:
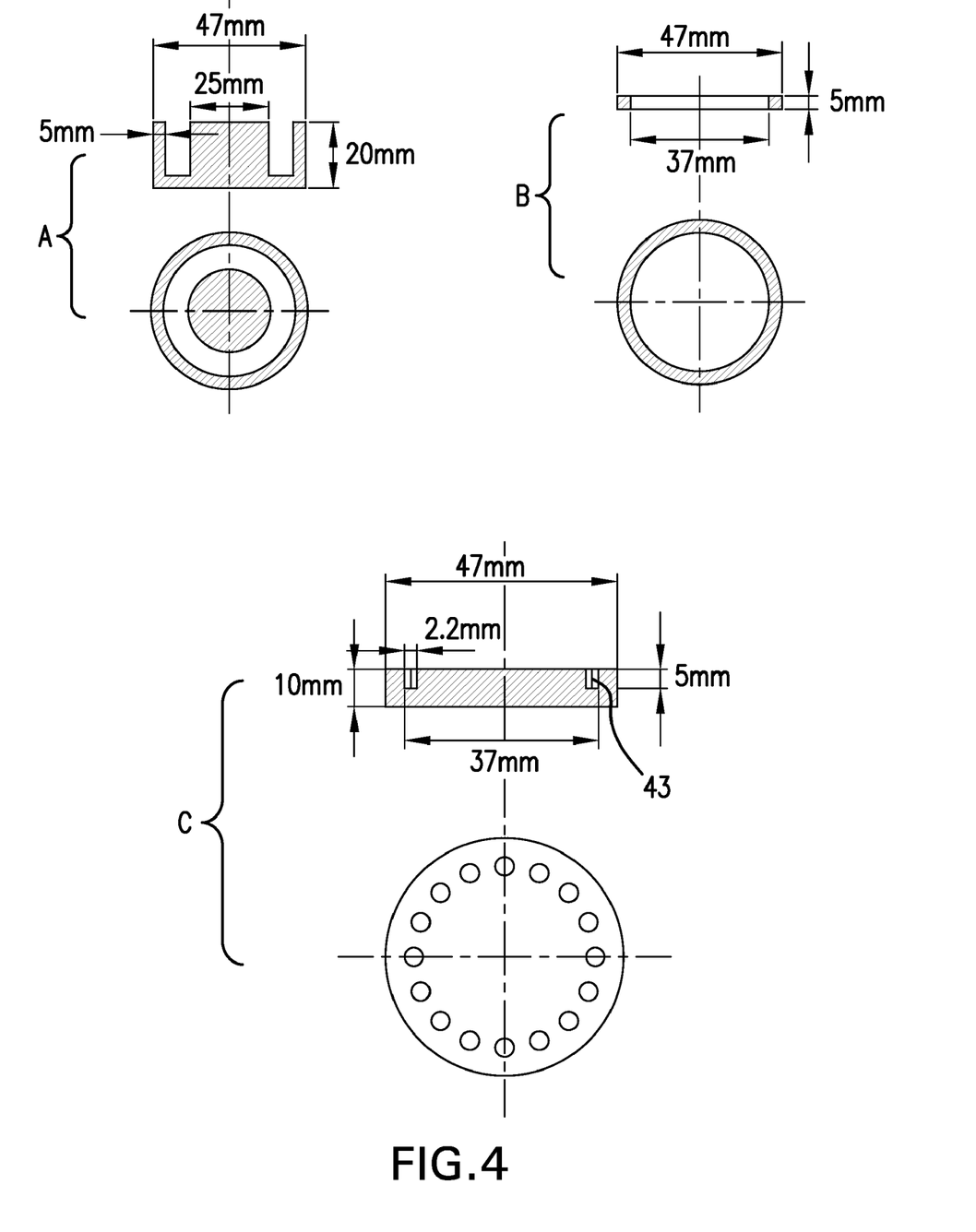
FIGS. 4A, 4B, and 4C are schematic top and side illustrations of different parts of a typical cylindrical shell Teflon/metal cell according to the invention, with FIG. 4A being the TEFLON cell, FIG. 4B being the TEFLON insulator and FIG. 4C being the 16-stent cell cover.

In another example, a cylindrical cell with a narrow thoroidal electrolyte compartment, including a shell or cover made with polymer material (body) metal and of metal (cover with stent holders are mounted) is used to contain a plurality of stents (FIG. 4A, FIG. 4B, FIG. 4C). A TEFLON® or similar polymer provides insulation around the cell such that a plurality of stents can be electroplated with a small amount of a plating solution. Depending on the size of the cell, about 10 or more, preferably about 15 or more stents, can be electroplated together. The size of the cell can be enlarged as needed, to simultaneously plate an even greater number of stents. Two circular Pt anodes are inserted in the TEFLON cell. In a further example, the cover of the cell is made of metal, such as brass, and includes holes 43 or body members to which a holding device for holding implants can be attached during the plating. For instance, the cover can include holes 43 into which top portions of a holding device can be screwed in, so that the holding device hangs from the cover during electroplating. The design of the cell can also be modified such that Ar or $N_2$ bubbling can be provided to every stent or every few stents by using a manifold gas distributor in the cell's center.

Figure 5:
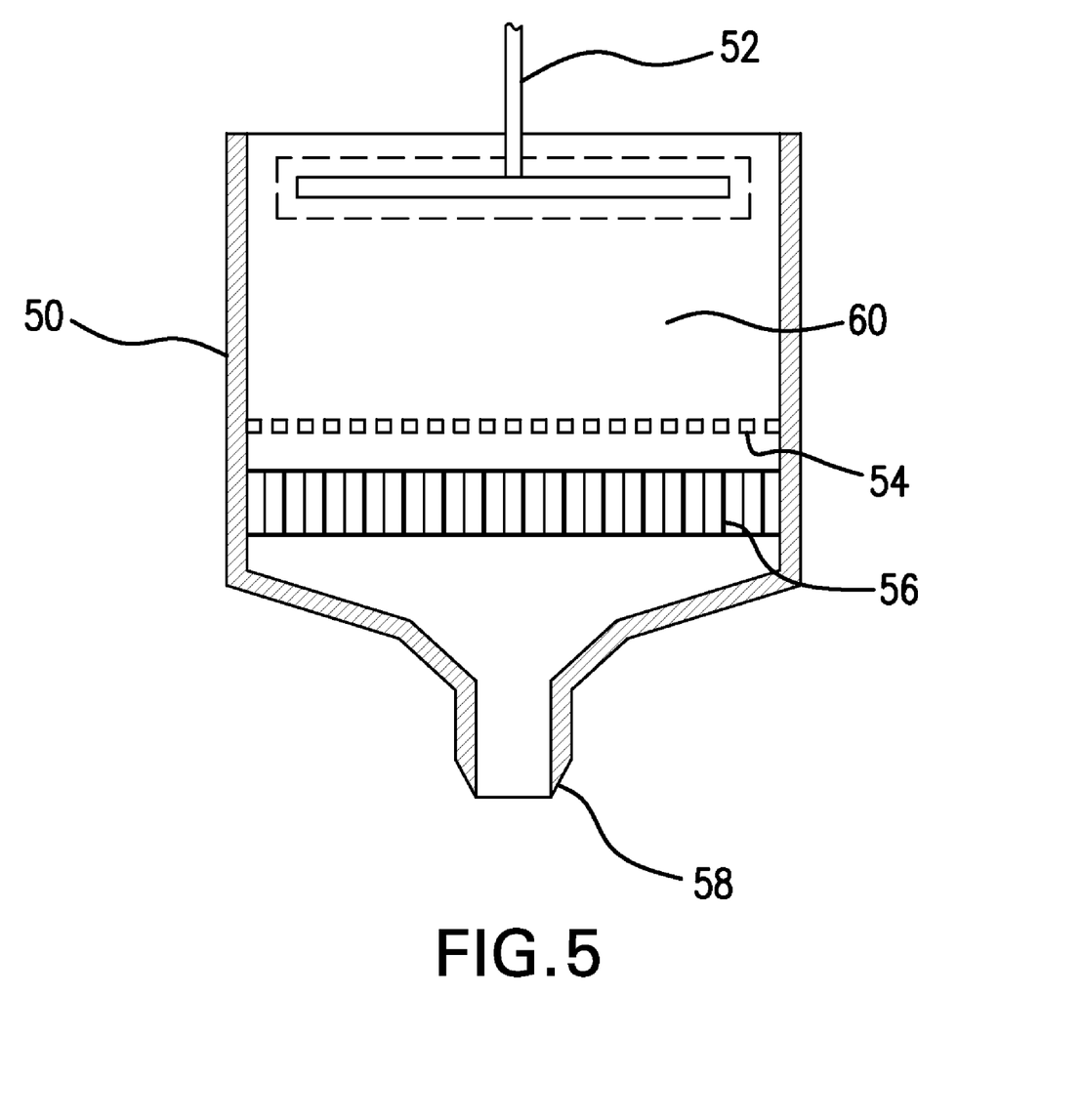
FIG. 5 is a schematic illustration of a slurry electroplating cell for plating a large number of stents according to the invention.

In yet another example, a slurry cell is used to plate a very large number of implants. In a slurry cell, implants are moved around the solution by Ar or $N_2$ bubbles and collide with one another and with the cathode. As shown in FIG. 5, a slurry cell 50 comprises an anode 52 in a porous separator, a cathode, which can be provided as a coarse cathode net 54, a coarse fritte 56, and a passage 58, through which Ar or $N_2$ bubbling is provided. When implants are added to the cell, the implants are moved around in the electrolyte 60.

The electroplating methods according to the invention provide a simple and effective electrodeposition of the CEES and overcome the difficulties observed in electroplating implants with a CEES in a conventional process. Further, by allowing selective and differential electrodeposition, the methods also enable selective radiotherapy.

Although luminal stents are often described in the above description and in the following examples as an exemplary implant that can be prepared according to the invention, a skilled artisan will appreciate the applicability of the invention to a wide variety of medical devices used to provide radiotherapy. For example, in addition to stents used to prevent and treat restenosis and various other cardiovascular or luminal conditions, implants prepared according to present methods can be used to treat constrictive cancers, such as cancers in the in the esophagus, gall bladder, biliary, renal and transhepatic system, and prostate.

EXAMPLES

The above description and the following examples are illustrative only and are not restrictive or limiting.

Example 1

Preparation of Stents Plated with Sn-117m without Seed Layer

Stents having a stainless steel scaffold are first thoroughly rinsed with acetone or ethyl alcohol (with sonication if needed) to remove any adventitious grease and dust particles. The implant is immersed for about 30 to 100 seconds in 1M HCl. After immersion, the implant is rinsed with water and alcohol or by applying $H_2$ evolution in $H_2SO_4$ to reduce remaining oxides in 0.1M $H_2SO_4$, for about 1 min at a current of 30 mA per stent.

Alternatively, activation involves, anodic activation in 1M $H_2SO_4$ with a current of 50 mA/cm$^2$: during 60 sec, followed by immersion in 1M HCl during 20 sec and cathodic reduction in 1M $H_2SO_4$ at 25 mA/cm$^2$, 30 sec. After rinsing by water or alcohol, tin is deposited.

The electroplating solution comprises about $1 \times 10^{-5}$ to $1 \times 10^{-2}$M Sn$^{2+}$, about 0.1 to 6M HCl, about 0.1 to 1M $H_2SO_4$, and about 1 to 10 g/l of at least one of resorcinol and gelatin, with the electroplating being performed with a current density of 5 to 100 mA/cm$^2$ for 0.5 to 5 minutes at room temperature.

Example 2A

Preparation of Stents Plated with Sn-117m Over a Cobalt Seed Layer

Stents having a stainless steel scaffold are first thoroughly rinsed with acetone or ethyl alcohol (with sonication if needed) to remove any adventitious grease and dust particles. The stents are then submerged in a solution containing 1 M HCl and 0.5 M CoCl$_2$ to provide activation and to plate a cobalt seed layer, with a current density of 5 to 10 mA/cm$^2$ for about 1 to 3 min. Cobalt deposition is followed by quick rinsing with water. The stents are then transferred to a Sn plating solution, to which the potential is quickly applied to avoid significant dissolution of Co. The Sn plating solution comprises (1 to 8)$\times 10^{-3}$M Sn$^{2+}$, 0.2 M $H_2SO_4$, 0.1 M HCl, and 2 g/l of resorcinol. The electroplating is carried out at room temperature with either potentiostatic or galvanostatic deposition at the potential E=–0.5 to –0.55V vs. Ag/AgCl/Cl$^-$ reference electrode and the current density of 0.1 to 0.5 mA/cm$^2$. Optionally, $10^{-7}$ to $10^{-2}$M Tl is added to the plating solution to reduce the rate of $H_2$ evolution.

Example 2B

Preparation of Stents Plated with Sn-117m Over a Nickel Seed Layer

Stents having a stainless steel scaffold are first thoroughly rinsed with acetone or ethyl alcohol (with sonication) to remove any adventitious grease and dust particles. The stents are then submerged in a solution containing 2M HCl and 0.1 to 0.2 M NiCl$_2$ to provide activation and to plate a nickel seed layer, with a current density of 5 to 15 mA/cm$^2$ for about 1 to 3 min.

Nickel deposition is followed by quick rinsing with water. The stents are then transferred to a Sn plating solution and the potential is quickly applied to avoid significant dissolution of Ni. The Sn plating solution comprises 2M HCl, $1 \times 10^{-2}$M Sn$^{2+}$, 0.2 M $H_2SO_4$, and 2 g/l of gelatin. The electroplating is carried out at room temperature with either potentiostatic or galvanostatic deposition at the potential E=–0.5 to –0.55V vs. Ag/AgCl/Cl$^-$ reference electrode and the current density of 0.1 to 0.5 mA/cm$^2$. Optionally, $10^{-7}$ to $10^{-2}$M Tl is added to the plating solution to reduce the rate of $H_2$ evolution.

Example 3

Preparation of $^{117m}$Sn

Tin-117m was prepared by the following typical process at the SM reactor at the Research Institute of Atomic Reactors (RIAR) in Dimitrovgrad, Russia: (i) dissolution of reactor-irradiated tin-117 metal; (ii) purification of $^{117m}$Sn using anion exchange and cementation; and (iii) dissolution of the deposited tin metal in hydrochloric acid in the presence of an oxidizing agent ($H_2O_2$) to ensure its conversion to the desired chemical form ($SnCl_4$). The prepared $^{117m}SnCl_4$ had $^{117m}Sn$ specific activity of 685 GBq/g (18.5 Ci/g), and the total gamma emitters to tin-117m activity ratio was ≦0.013%. The hydrochloric acid solvent concentration was 8 mol/l.

Four 0.5 Ci samples of the preparation were prepared for analysis. The specific activity of tin-117m on the delivery date was 10.1 Ci/g and the total activity of radioactive impurities (excluding $^{113}Sn+^{113m}In$) was 0.0004%, relative to the activity of $^{117m}Sn$.

Several experimental targets were prepared and irradiated to determine the optimum irradiation conditions that were adopted in the final methodology as described above. A cadmium shield with a thickness of 1.5 mm was used as a construction element. The target was irradiated in cell N 55 of the active core of the SM reactor for 24.3 effective days. The results of the radionuclidic impurities in the Sn-117m solution are summarized in Table 1. When compared to a target irradiated without a cadmium shield, no considerable differences in yields of radioactive impurities were observed.

TABLE 1

| Relative activities of impurity radionuclides and Sn-117m activity (%) | | | | | |
|---|---|---|---|---|---|
| Sn-113 | Sn-125 | Sb-122 | Sb-124 | Sb-125 | Sb-126 |
| 4.3E−03 | 1.4E−04 | 5.7E−02 | 4.1E−03 | 3.1E−03 | 2.1E−03 |
| Co-58 | Co-60 | Se-75 | Mn-54 | Fe-59 | Zn-65 |
| 1.1E−02 | 2.0E−04 | ≦8.0E−05 | 3.5E−04 | 4.2E−04 | ≦3.5E−04 |

As used herein, the term "about" should generally be understood to refer to both the corresponding number and a range of numbers. All numerical ranges herein should be understood to include each whole integer within the range. While illustrative embodiments of the invention are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the invention.

What is claimed is:

1. A method of electroplating an implant with a deposit containing tin-117m, which method comprises:
   combining tin-117m with cold tin in a solution to provide a total tin concentration in the range of $1\times10^{-5}$ to $1\times10^{-2}$ M;
   converting the tin in the solution to $Sn^{+2}$ ions with the cold tin and tin-117m ions homogeneously distributed in the solution;
   immersing the implant in the solution; and
   applying a current to the implant effective to cause the $Sn^{+2}$ ions to electroplate the implant and provide thereon an electroplated implant that includes a deposit that contains tin-117m and cold tin,
   wherein the electroplated implant provides radioactive emissions of from 0.02 mCi/mm to 10 mCi/mm.

2. The method of claim 1, which further comprises activating a surface of the implant to receive the deposit; and contacting the activated surface of the implant with the tin solution.

3. The method of claim 2, wherein the activating solution comprises hydrochloric acid; and the tin solution comprises HCl, $H_2SO_4$, phenol-sulfonic acid, a surfactant and an antioxidant.

4. The method of claim 3, wherein the HCl is present in an amount of about 0.1 to 6M, the $H_2SO_4$ is present in an amount of about 0.1 to 1 M, the surfactant is gelatin and the antioxidant is resorcinol with the surfactant and antioxidant each present in an amount of about 1 to 10 g/l.

5. The method of claim 1, which further comprises providing $H_2$ evolution during the electroplating for diffusion control.

6. The method of claim 5, which further comprises controlling $H_2$ evolution by adding thallium ($Tl^+$) to the plating solution in a concentration range of between $10^{-2}$ M and $10^{-2}$ M.

7. The method of claim 1, which further comprises protecting the electroplated implant by passivating the deposit.

8. The method of claim 1, which further comprises protecting the deposit on the implant by providing a protective film thereon.

9. The method of claim 8, wherein the protective film comprises alkene thiol, methyl methacrylate, or a noble metal.

10. The method of claim 1, wherein the implant is a metal stent and the electroplated implant emits about 0.125 to 0.75 mCi/mm of radiation to an emission distance of about 0.2 to 0.3 mm.

11. The method of claim 10, wherein the stent is made of stainless steel, $^{115}Sn$, a shape-memory alloy, or a combination thereof.

12. The method of claim 1, which further comprises selectively applying the CEES coating on the surface of the implant.

13. The method of claim 12, which further comprises mounting the implant on a holding device to assist in providing the selective CEES coating by preventing electroplating on portions of the exposed surface of the implant.

14. The method of claim 13, wherein the implant is a stent having interior and exterior surfaces and contacts the holding device along its entire interior surface such that only the exterior surface of the stent is electroplated.

15. The method of claim 14, wherein the holding device comprises a body and at least two elongated arms extending from the body, wherein the outer perimeter of the device around the arms is configured to generally conform to the interior surface of the implant.

16. The method of claim 1, which further comprises polishing or stabilizing the deposit of $^{117m}Sn$ by annealing the electroplated implant in an atmosphere of argon or nitrogen at a temperature of about 100 to 300° C.

* * * * *

UNITED STATES PATENT AND TRADEMARK OFFICE
CERTIFICATE OF CORRECTION

PATENT NO.        : 8,114,264 B2
APPLICATION NO.   : 11/758914
DATED             : February 14, 2012
INVENTOR(S)       : Suresh Srivastava et al.

It is certified that error appears in the above-identified patent and that said Letters Patent is hereby corrected as shown below:

Col. 3, line 7, "several orders of magnitude than"     should read: --several orders of magnitude less than--

Col. 4, lines 5-6, "when the implant is placed in a body lumen, thus avoid damage"     should read: --when the implant is placed in a body lumen, thus avoiding damage--

Col. 4, line 39, "encircles the aims"     should read: --encircles the arms--

Col. 11, line 57, "(from side-aim-to-side-arm)"     should read: --(from side-arm-to-side-arm)--

Col. 12, line 58, "be used instead of mandrel."     should read: --be used instead of a mandrel.--

Col. 16, line 11, CLAIM 4, "wherein the HC1 is"     should read: --wherein the HCl is--

Col. 16, line 21, CLAIM 6, "wherein the HC1 is"     should read: --wherein the HCl is--

Signed and Sealed this
Nineteenth Day of June, 2012

David J. Kappos
*Director of the United States Patent and Trademark Office*